(12) United States Patent
Enghild et al.

(10) Patent No.: US 6,300,088 B1
(45) Date of Patent: Oct. 9, 2001

(54) METHOD OF DETECTING PROSTATE SPECIFIC ANTIGEN

(75) Inventors: Jan J. Enghild, Durham, NC (US); Tim D. Oury, Wexford, PA (US); Ida B. Thogersen, Durham, NC (US); Zuzana Valnickova, Durham, NC (US); Philip J. Walther, Durham, NC (US)

(73) Assignee: Duke University, Durham, NC (US)

( * ) Notice: Subject to any disclaimer, the term of this patent is extended or adjusted under 35 U.S.C. 154(b) by 0 days.

(21) Appl. No.: 09/193,263

(22) Filed: Nov. 18, 1998

Related U.S. Application Data

(60) Provisional application No. 60/066,497, filed on Nov. 24, 1997.

(51) Int. Cl.[7] .................. G01N 33/574; A61K 38/04; C07K 16/00; C07K 17/00; C07K 5/00
(52) U.S. Cl. .................. 435/7.23; 530/329; 530/300; 435/4; 435/7.1; 435/7.21; 436/64
(58) Field of Search .................. 530/300, 329, 530/387.1; 435/4, 7.1, 7.21, 7.23; 436/64

(56) References Cited

U.S. PATENT DOCUMENTS

| Re. 33,405 | 10/1990 | Chu et al. .................. 530/350 |
| 4,446,122 | 5/1984 | Chu et al. .................. 424/1.1 |
| 5,356,781 | 10/1994 | Hermon-Taylor et al. .......... 435/4.9 |
| 5,501,983 | 3/1996 | Lilja et al. .................. 436/518 |
| 5,506,106 | 4/1996 | Croce et al. .................. 435/6 |
| 5,543,296 | 8/1996 | Sobol et al. .................. 435/6 |
| 5,599,677 | 2/1997 | Dowell et al. .................. 435/7.4 |
| 5,648,478 | 7/1997 | Henderson .................. 536/241 |
| 5,654,161 | 8/1997 | Tewari .................. 435/7.23 |
| 5,658,730 | 8/1997 | McGill et al. .................. 435/6 |
| 5,672,480 | 9/1997 | Dowell et al. .................. 435/7.4 |
| 5,688,658 | 11/1997 | Diamandis .................. 435/7.23 |
| 5,723,302 | 3/1998 | Diamandis .................. 435/7.1 |
| 5,817,481 | 10/1998 | Rood .................. 435/69.1 |

FOREIGN PATENT DOCUMENTS

| WO 97/32215 | 9/1997 | (WO) . |
| WO 98/49323 | 11/1998 | (WO) . |

OTHER PUBLICATIONS

Reissigl et al., "Improvement of Prostate Cancer Screening by Determination of the Ratio Free/Total PSA in Addition to PSA Levels," Prostate, 30(4), Mar. 1, 1997, pp. 243–247.

(List continued on next page.)

*Primary Examiner*—Yvonne Eyler
*Assistant Examiner*—Jennifer Hunt
(74) *Attorney, Agent, or Firm*—Myers Bigel Sibley & Sajovec

(57) ABSTRACT

Dectection of secreted Prostate Specific Antigen (PSA) by detecting the presence of an N-terminal activation peptide of PSA in a biological sample is described. The method may be used in screening for or diagnosing disease states associated with increased levels of secreted prostate specific antigen.

28 Claims, 4 Drawing Sheets

OTHER PUBLICATIONS

Marachal et al., "PSA and PS2 Expression in Prostatic Tissue," Cancer Detec. Prevent., 20(5), Abstract, 1996, p. 514.

Belanger et al., "Molecular Mass and Carbohydrate Structure of Prostate Specific Antigen: Studies for Establishment of an International PSA Standard," Prostate, 27(4), 1995, pp. 187–197.

Leinomen et al., "Double–Label Time–Resolved Immunofluorometric Assay of Prostate–Specific Antigen and of Its Complex with $\alpha_1$–Antichymotrypsin," Clin. Chem., 39(10), 1993, pp. 2098–2103.

Lundwall et al., "Molecular cloning of human prostate specific antigen cDNA," Febs. Lett., 214(2), 1987, pp. 317–322.

Lilja et al., "Prostate Specific Antigen Predominantly Forms a Complex with Alpha$_1$–Antichymotrypsin in Blood," Cancer, 70 (1 Suppl), 1992, pp. 230–234.

Partin et al., "The Clinical Usefulness of Prostate Specific Antigen: Update 1994," J. Urology, 152, (5 pt 1) 1994, pp. 1358–1368.

Stenman et al., "A Complex between Prostate–specific Antigen and $\alpha_1$–Antichymotrypsin Is the Major Form of Prostate–specific Antigen in Serum of Patients with Prostatic Cancer: Assay of the Complex Improves Clinical Sensitivity for Cancer," Cancer Res., 51(1), 1991, pp. 222–226.

Takayama et al., "Characterization of the Precursor of Prostate–specific Antigen," J. Biol. Chem, 272, 1997, pp. 21582–21588.

Woolf, "Screening for Prostate Cancer with Prostate–Specific Antigen," N. Engl. J. Med., 333, 1996, pp. 1401–1405.

Zhou et al., "Multiple Forms of Prostate–Specific Antigen in Serum: Differences in Immunorecognition by Monoclonal and Polyclonal Assays," Clin. Chem., 39(12), 1993, pp. 2483–2491.

Mikolajczyk et al., "A Precursor Form of PSA (pPSA) is a Component of the Free PSA in Prostate Cancer Serum," Urology, 50(5), 1997, pp. 710–714.

Zarghami et al., "Detection of prostate–specific antigen mRNA and protein in breast tumors," Clinical Chemistry, 42(3), Mar. 1996, pp. 361–366.

Lehrer et al., "Reverse transcriptase–polymerase chain reaction for prostate–specific antigen may be a prognostic indicator in breast cancer," British J. Cancer, 74, Sep. 1996, pp. 871–873.

Lai et al., "Prostate–Specific Antigen in Breast Cyst Fluid: Possible Role of Prostate–Specific Antigen in Hormone–Dependent Breast Cancer," Int. J. Cancer, 66, 1996, pp. 743–746.

Saedi et al., "The precursor form of the human kallikrein 2, a kallikrein homologous to prostate–specific antigen, is present in human sera and is increased in prostate cancer and benign prostatic hyperplasia," Clinical Chemistry, 44(10), 1998, pp. 2115–2119.

International Search Report, PCT/US98/25054, May 21, 1999.

Activation Peptide alone

Prostate cancer patients

URINE

SERUM

Control patients

SEQUENCE LISTING

<160> NUMBER OF SEQ ID NOS: 2

<210> SEQ ID NO 1
<211> LENGTH: 7
<212> TYPE: PRT
<213> ORGANISM: Homo sapiens

<400> SEQUENCE: 1

Ala Pro Leu Ile Leu Ser Arg
 1               5

<210> SEQ ID NO 2
<211> LENGTH: 8
<212> TYPE: PRT
<213> ORGANISM: Homo sapiens

<400> SEQUENCE: 2

Ala Pro Leu Ile Leu Ser Arg Cys
 1               5

METHOD OF DETECTING PROSTATE SPECIFIC ANTIGEN

This application claims the benefit of US Provisional application Ser. No. 60/066,497, filed Nov. 24, 1997.

This invention was made with Government support under National Institutes of Health Grants HL-49542. The Government has certain rights to this invention.

FILED OF THE INVENTION

The present invention relates to methods of detecting Prostate Specific Antigen in a subject by detection of an activation peptide that is cleaved from the PSA proenzyme. Such methods aid in the detection, diagnosis and prognosis of diseases, including prostate disease and breast cancers.

BACKGROUND OF THE INVENTION

More than 1.3 million new cases of invasive cancer are expected to be diagnosed in the United States during 1997 (Parker et al. *CA Cancer J. Clin.* 47:5 (1997); this estimate does not include carcinoma in situ (except in the bladder), nor does it include basal and squamous cell cancers of the skin). Among women, it is estimated that the three most commonly diagnosed cancers in 1997 will be cancers of the breast, lung and bronchus, and colon and rectum. Breast cancer alone will account for 30% of new cancer cases in 1997. Among men, the most common cancers in 1997 will be cancers of the prostate, lung and bronchus, and colon and rectum, with prostate being the leading cancer site and accounting for 43% of new cancer cases.

Prostate cancer accounts for 36% of all male cancers and 13% of male cancer-related deaths (surpassed only by lung cancer). It is estimated that approximately 334,500 new cases of prostate cancer and 41,800 prostate cancer-related deaths will occur in the United States in 1997. Incidence rates of prostate cancer have increased over the past 35 years. Parker et al. *CA Cancer J. Clin.* 47:5 (1997). Screening for prostate cancer has traditionally relied on digital rectal screening. Transrectal ultrasound and measurement of prostate-specific antigen (PSA) in the blood have also recently become available to aid in the diagnosis of prostate cancer. See, e.g., Friedman et al., *Lancet* 337:1526 (1991); Littrup, *Cancer* 74 (7 Suppl):2016. However, the cost, relatively low specificity, and invasiveness of rectal imaging techniques precludes these from use in routine or large-scale screening for prostate cancer. Additionally, the effectiveness of such techniques are non-specific and depend on the skill and experience of the examiner. Waterhouse and Resnick, *J. Urol.* 141:233 (1989); Waterhouse and Resnick, *Urology*, 36:18 (1990).

Benign Prostate Hypertrophy (BPH) is a common condition in men over the age of 50, and occurs in the majority of men over the age of 80. BPH and prostate cancer may occur simultaneously in a subject.

It is estimated that in 1997 breast cancer will account for 30 percent of new cancer cases, with about 180,200 new cases diagnosed. Parker et al. *CA Cancer J. Clin.* 47:5 (1997). Diagnosis of breast cancer typically depends on physical examination of the breast and/or routine mammography, with subsequent ultrasound and/or biopsy as indicated.

Due to the known association of PSA with diseases such as BPH and prostate and breast cancers, and the high incidence of such diseases, it would be advantageous to develop effective and convenient methods of screening for the presence of cancer.

SUMMARY OF THE INVENTION

A first aspect of the present invention is a method of screening a subject for secreted Prostate Specific Antigen (PSA), comprising obtaining a biological sample from a subject and detecting the amount of PSA activation peptide in the sample.

A further aspect of the present invention is a method of screening a subject for the presence of a condition associated with an increased level of secreted Prostate Specific Antigen (PSA), comprising obtaining a biological sample from a subject, detecting the amount of PSA activation peptide in the sample, and comparing the amount of peptide detected to a pre-determined standard. Detection of a level of peptide greater than that of the standard indicates the presence of the condition for which the screening is being carried out.

A further aspect of the present invention is a method of screening a subject for prostate disease, comprising obtaining a urine sample from the subject, and detecting the presence of PSA activation peptide in the sample. The presence of PSA activation peptide in the sample is indicative of prostate disease.

A further aspect of the present invention is an immunoassay method for determining the presence of a peptide of SEQ ID NO:1 in a sample, comprising obtaining a test sample, exposing the sample to an antibody specific for a peptide of SEQ ID NO:1; and detecting the binding of antibody to peptides present in the sample. Binding of antibodies indicates the presence of peptides of SEQ ID NO:1 in the sample.

A further aspect of the present invention is a method of screening for prostate cancer in a subject, comprising obtaining a biological sample (urine, blood, blood plasma or blood serum) from the subject, and detecting the presence of PSA activation peptide in the sample. The presence of the peptide is indicative of prostate cancer in the subject.

A further aspect of the present invention is an isolated peptide of SEQ ID NO:1.

A further aspect of the present invention is an antibody or antibody fragment that specifically binds to a peptide of SEQ ID NO:1.

DETAILED DESCRIPTION OF THE INVENTION

Figure 1:
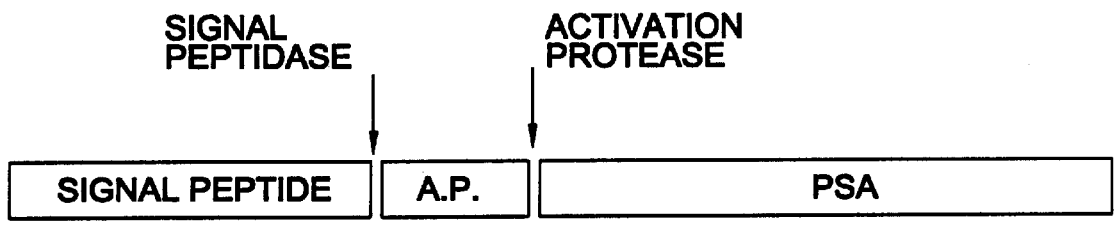
FIG. 1 is a schematic drawing of the pro-PSA molecule, where "a.p." indicates the activation peptide and "PSA" indicates the mature active PSA molecule. The arrows indicate the positions of the expected proteolytic cleavage sites.

Measurement of the level of serum prostate-specific antigen (PSA) in the blood or serum is an accepted screening test for prostate cancer. This procedure has been utilized both for initial diagnosis and to monitor the effectiveness of therapy. Babian et al., *Cancer*, 69:1195 (1992); Partin and Oesterling, *J. Urol.*, 152:1358–1368 (1994); Brawer et al., *J. Urol.* 147:841 (1992); Catalona et al., *JAMA* 270:948 (1993); Mettlin et al., *Cancer* 72:1701 (1993).

PSA is a glycosylated serine protease with an apparent molecular mass of approximately 36 kDa. The predicted protein sequence is a 237 amino acid protein with a calculated molecular mass of 26.1 kDa. The difference between the observed and calculated mass is attributed to one N-linked oligosaccharide attached to As$_{45}$. Belanger et al., *Prostate* 27:187 (1995). Analysis of the amino acid sequence indicates that PSA is a member of the chymotrypsin family of serine proteases. Serine proteases are synthesized as precursors, and activated by the removal of an N-terminal activation peptide. In certain serine proteases (e.g., human neutrophil elastase and cathepsin G), the activation peptide is removed before secretion of the protease; in other cases (e.g., thrombin and trypsin), the activation peptide is removed extracellularly, after secretion.

A recent study of the activation of recombinant pro-PSA seems to support the hypothesis that PSA is processed similar to other extracellular proteases. Takayama et al., *J. Biol. Chem.* 272:21582 (1997). See also Gauthier et al., *Biochim. Biophys. Acta* 1174:207 (1993); Lilja, *J. Clin. Invest.* 76:1899 (1985); Lundwall and Lilja, *FEBS Lett.* 214:317 (1987); Schaller et al., *Eur. J. Biochem.* 170:111 (1987).

In blood, PSA is found in three forms: (i) free-PSA; (ii) PSA•α1-antichymotrypsin complexes (PSA•α1-ACT) and (iii) PSA•α2-macroglobulin complexes (PSA•α2M). Leinonen et al., *Clin. Chem.* 39:2098 (1993); Stenman et al., *Cancer Research* 51:222 (1991). Of these three major serum forms, only free-PSA and PSA•α1-ACT are immunodetectable by current commercial assays. PSA•α2M complexes are not recognizable by the antisera because of the unique nature of the complex. Barrett and Starkey, *Biochem. J.* 133:709 (1973); Barrett et al., *Biochemical J.* 181:401 (1979). These three forms are considered to represent total PSA in serum, even though trace amounts of PSA complexes to intera-trypsin inhibitor (IαI) and α1-protease inhibitor (α1PI) have been reported. Stenman et al., *Cancer Res.* 51:222 (1991).

Studies of the various PSA forms in serum suggest that the mean proportion of PSA•α1-ACT is higher in patients with prostate cancer than in patients with benign prostate hypertrophy (BPH), although an overlap occurs between the two groups. Christensson et al., J. Urol. 150:100 (1993); Stenman et al. *Cancer Research* 51:222 (1991). It has been proposed that calculating the ratio of PSA•α1-ACT/total-PSA may provide a way to discriminate prostate cancer and BPH. Leinonen et al., *Clin. Chem.* 39:2098 (1993). Lilja and coworkers reported that PSA•α1-ACT is the major form of circulating PSA (Lilja et al., *Clin. Chem.* 37:1618 (1991); Lilja et al., *Cancer* 70(1 Suppl):230 (1992)); their further work demonstrated that the ratio of PSA•α1-ACT/total-PSA was significantly higher in patients with prostate cancer than in patients with BPH (Christensson et al., *J. Urol.* 150:100 (1993)).

Current use of PSA testing is directed toward detecting the three major PSA forms in the blood (free-PSA, PSA•α1-ACT, and PSA•α2M), as well as complexes of PSA with other serine protease inhibitors including IαI and α1PI. However, the use of PSA as a screening or diagnostic test for the presence of prostate cancer suffers from several limitations. PSA interacts with several other proteins in the blood. These interactions affect the half-life of PSA in the blood and interfere (and may even prevent) detection. Additionally, PSA•α2M complexes are not detected (Lilja et al., *Clin. Chem.* 37:1618 (1991), Zhou et al., *Clin. Chem.* 39:2483 (1993)). Benign conditions may cause an elevated serum PSA level, resulting in unnecessary biopsies or additional testing; it is also true that some prostate cancers are associated with normal serum PSA concentrations.

Further, as discussed herein, the rapid removal of PSA from the circulation in the early stages of disease is a heretofore unrecognized problem with conventional PSA testing. While not wishing to be held to a single hypothesis, the present inventors believe that where prostate cancer is associated with a normal serum PSA concentration, the plasma elimination mechanism of PSA has not yet been exhausted, so that secreted PSA is quickly removed from the bloodstream and a normal serum PSA level is maintained. This clearance rate is likely to depend on the overall health of the patient, including physical condition, body weight, and alcohol and tobacco consumption. These factors may affect the half-life of PSA forms in the blood but should not significantly affect the half-life of the activation peptide. As discussed herein, the removal of the activation peptide is a passive process not dependent on the reaction of the activation peptide with other peptides, and subsequent endocytosis.

PSA is produced by many different tissues in the body and has been shown to be present in low concentrations in breast milk. PSA has also been detected in about 30% of breast cancers. Monne et al., *Cancer Research* 54:6344 (1994); Yu et al., *Clin. Biochem.* 27:75 (1994); Yu et al., *Cancer Research* 55:2104 (1995); Diamandis et al., *Breast Cancer Res. Treatment* 32:301 (1994). Lehrer et al. (*Brit. J. Cancer* 74:871 (1996)) reported detecting a PSA fragment in the blood of 18 of 78 women with breast cancer (using PCR to amplify a fragment of the PSA molecule). These authors concluded that their PCR-based test could be used to find circulating cancer cells early in the course of breast cancer, to identify patients requiring additional treatment. Zarghami and Diamandis (*Clin. Chem.* 42:361 (1996)) reported that, using PCR-based tests, PSA mRNA and protein were detected in breast tumor tissue.

The present inventors have shown by sequence analysis of the secreted PSA molecule that PSA is secreted as an inactive pro-enzyme or zymogen, with an attached N-terminal activation peptide. Cultured human prostate cancer cells (LNCAP cells) were found to secrete pro-PSA containing a 7-residue N-terminal activation peptide of sequence Ala-Pro-Leu-Ile-Leu-Ser-Arg (SEQ ID NO:1) (see Example 2 herein). The present inventors have shown that the activation peptide is cleaved from pro-PSA outside of the cell, where it can be detected, rather than inside the cell where it would likely be degraded. The present inventors believe that the sequence of the PSA activation peptide will be highly conserved, however it is possible that variants of the PSA activation peptide of SEQ ID NO:1 may occur. PSA activation peptide variants arising by conservative amino acid substitution, or having substantial sequence similarity to SEQ ID NO:1, are also encompassed within the scope of the present invention.

In addition, the present inventors have shown in an in vivo animal model that when a small amount of PSA is introduced into the blood stream it quickly reacts with specific protease inhibitors and is removed from blood circulation by binding to hepatocyte receptors and subsequent endocytosis (see Example 3 herein). While not wishing to be held to a single theory, the present inventors infer that in early stages of cancer PSA secretion may be limited and, due to the reaction of PSA with protease inhibitors, PSA may be rapidly eliminated from the blood stream and thus undetectable for diagnostic purposes. The present inventors surmise that as cancer progresses and increased levels of PSA are released into the blood stream, the plasma elimination mechanisms are overwhelmed and PSA complexes begin to accumulate in the blood (see FIG. 3), allowing detection of PSA in the blood for diagnostic purposes.

The present inventors have discovered that (i) PSA is secreted as a proenzyme (pro-PSA) containing an N-terminal activation peptide; (ii) that PSA in the blood does not react with pro-PSA antisera and therefor has been activated; (iii) the plasma elimination kinetics of PSA suggest that PSA accumulates in the blood when the clearance mechanism has been saturated; (iv) plasma elimination of the activation peptide indicates filtration out of the blood by the kidney; and (v) the activation peptide is detectable in urine and in blood.

The present inventors identified the sequence of the N-terminal activation peptide of PSA produced by cultured human prostate cancer cells (LNCAP cells) as Ala-Pro-Leu-Ile-Leu-Ser-Arg (SEQ ID NO:1). The present results indicate that the presence of the PSA activation peptide (e.g., peptide of SEQ ID NO:1) in urine or blood is a reliable indicator of secreted PSA in a subject. The activation peptide is cleaved from PSA during activation of pro-PSA and apparently does not interact with other proteins, but is cleared from the blood by simple renal filtration. The activation peptide is consequently easy to detect by assaying for its presence in the urine by any suitable method. Because the presence of the PSA activation peptide indicates the presence of secreted PSA, screening for the presence of the activation peptide in urine provides a method of screening for cancers associated with increased levels of secreted PSA, including prostate cancers and breast cancers.

Thus, the present inventors have determined that PSA activation peptide can be detected in biologic samples from subjects, and that the level of PSA activation peptide is an indicator of secreted PSA. Accordingly, detection of PSA activation peptide is indicative of PSA secretion. Detection and or quantitative measurement of PSA activation peptide is therefore useful in screening for or detecting diseases associated with increases in PSA. Such conditions include BPH, prostate cancer and breast cancer. In a preferred embodiment of the present invention, the condition for which the screening test is carried out is breast cancer, and the sample being screened is urine or blood. In a further preferred embodiment of the present invention, the condition for which the screening test is carried out is prostate cancer, and the sample being screened is urine or blood.

As used herein, an "increased level" of PSA activation peptide refers to a level that is increased over a predetermined standard, or increased over the level in a control sample. The pre-determined standard may be based on the detection of PSA activation peptide in healthy subjects, and may be zero or undetectable. Alternatively, in testing a subject, the pre-determined standard may be based on an earlier test result of the same subject, i.e., the test results may be followed over time to detect changes in PSA activation peptide. PSA testing is known to be useful in detecting metastatic or persistent disease in patients following medical or surgical treatment of prostate cancer, where persistent elevation of (or increases in) PSA levels following treatment indicates recurrent or residual disease. The level of PSA activation peptide that is considered as an indicator of disease may differ among the target diseases for which the screening method is used; the level of PSA activation peptide may be measured as an amount per unit of test sample, or as a percentage of the total protein in a test sample. The diagnostic or indicator level of PSA activation peptide for a particular disease state may be determined using routine clinical testing methods known in the art. Any number of protocols can be used to develop data for use in performing the diagnostic methods of the present invention; the methods and guidelines for developing suitable study protocols are known to those in the art.

The methods disclosed herein may be employed with subjects suspected of having a disease state associated with increased PSA levels, including but not limited to BPH, prostate cancer, and breast cancer. The present methods may be employed both to monitor subjects who have been previously diagnosed with the target condition, to monitor subjects undergoing treatment for the target condition, or to screen subjects who have not been previously diagnosed with the target condition, including asymptomatic subjects. Subjects include humans as well as mammalian veterinary subjects, and include both male and female subjects. The methods disclosed herein are particularly suited for screening for prostate cancer, and for aiding in the diagnosis and prognosis of prostate cancer.

As used herein, methods of screening and diagnosis do not mean that the methods are 100% specific or sensitive in indicating the presence of the target disease state; rather, a positive screening or diagnostic test indicates that the subject is at an increased risk (compared to the general population) of being afflicted with the target condition. In a sampling of multiple subjects, positive test results will be correlated with the presence of the target condition. The specificity and sensitivity of the present methods may vary depending on the condition being screened or monitored, the biological sample being screened, the general health of the subject being screened, and other factors, as will be apparent to those skilled in the art.

In a particular embodiment of the present invention, the subject has previously been diagnosed as having a disease associated with elevated PSA levels (such as prostate or breast cancer), and may have already undergone treatment for such disease. The present methods are suitable to monitor the recurrence or progression of the disease or the success of the treatment thereof; in such cases, the levels of PSA activation peptide in a subject may be compared over time.

Prostate cancer is a well recognized disease entity. As used herein, the term prostate cancer includes any histological type of cancer arising from prostate tissue. The most common tumor arising in the prostate is adenocarcinoma. Adenoid cystic carcinomas, carcinosarcomas, and sarcomas, as well as other histological types of cancers, may also occur in the prostate.

Breast cancer is a well recognized disease entity. As used herein, the term breast cancer includes any histologic type of cancer arising from breast tissue. Breast cancers most commonly arise from epithelium; other histologic types of mammary carcinoma have been described.

Benign Prostate Hypertrophy (BPH) is a common condition in men over the age of 50, and occurs in the majority of men over the age of 80. Treatment of BPH includes drug therapy to decrease prostate volume and surgical resection of the prostate. Increased serum concentrations of PSA are reported in BPH.

Samples taken from subjects for use in the methods disclosed herein are generally biological fluids such as urine, blood (including whole blood, blood serum and blood plasma), ascites fluid, cyst fluid (such as breast cyst fluid) or other body fluids that would contain the PSA activation peptide. In testing for prostate cancer, urine is a preferred test sample.

Methods of obtaining samples to be tested will be carried out according to techniques known in the art, and may depend on the condition being screened for and the condition of the subject. Samples may undergo additional conventional preparation steps prior to the detection of the PSA activation peptide, as will be apparent to those skilled in the art. For example, samples may undergo the addition of preservatives, concentrating steps, filtration, etc.

The levels of PSA activation peptide may be determined as an amount of peptide per volume of sample, or as a percentage of the total protein in the sample.

Antibodies which may be used to carry out the present invention include antibodies which bind specifically to a peptide of SEQ ID NO:1 and fragments of such antibodies, which fragments bind specifically to a peptide of SEQ ID NO:1. Such antibodies and antibody fragments may be produced by a variety of techniques, as discussed below.

The term "antibodies" as used herein refers to all types of immunoglobulins, including IgG, IgM, IgA, IgD, and IgE. Of these, IgM and IgG are preferred. The antibodies used in the present methods may be obtained in accordance with known techniques, and may be monoclonal or polyclonal, and may be of any species of origin, including (for example) mouse, rat, rabbit, horse, or human, or may be chimeric antibodies. See, e.g., M. Walker et al., *Molec. Immunol.* 26:403 (1989). The antibodies may be recombinant monoclonal antibodies produced according to the methods disclosed in Reading, U.S. Pat. No. 4,474,893, or Cabilly et al., U.S. Pat. No. 4,816,567. The antibodies may also be chemically constructed by specific antibodies made according to the method disclosed in Segel et al., U.S. Pat. No. 4,676,980. Antibody fragments included within the scope of the present invention include, for example, Fab, $F(ab')_2$, and Fv fragments, and the corresponding fragments obtained from antibodies other than IgG. Such fragments can be produced by known techniques.

Polyclonal antibodies used to carry out the methods of the present invention may be produced by immunizing a suitable animal (e.g., rabbit, goat, etc.) with the target antigen, collecting immune serum from the animal, and separating the polyclonal antibodies from the immune serum, in accordance with known procedures.

Monoclonal antibodies used in the present methods may be produced in a hybridoma cell line according to the technique of Kohler and Milstein, *Nature* 265:495 (1975) and other techniques known in the art. Monoclonal Fab fragments may be produced in *Escherichia coli* by recombinant techniques known to those skilled in the art. See, e.g., Huse, *Science* 246:1275 (1989).

The methods disclosed herein detect the presence of PSA activation peptide, which the present inventors have determined is indicative of the presence of activated PSA in the subject being tested. Any suitable method of detecting PSA activation peptide may be used, as would be apparent to one skilled in the art. Preferred detection methods are immunoassay formats, which may be homogeneous assays of heterogeneous assays. In a homogeneous assay the immunological reaction usually involves antibody against the PSA activation peptide, a labeled analyte (labeled PSA activation peptide) and the test sample of interest. The signal arising from the label is modified, directly or indirectly, by the binding of the antibody to the labeled analyte. Both the immunological reaction and detection of the extent of the immunological reaction are carried out in a homogeneous solution. Immunochemical labels that may be employed include free radicals, radioisotopes, fluorescent dyes, enzymes, coenzymes, etc.

In a heterogeneous assay approach, the reagents are usually the test sample, antibody specific for PSA activation peptide, and means for producing a detectable signal, as discussed above. The antibody is generally immobilized on a support (such as a bead, plate or slide) and contacted with the test sample in liquid phase. The support is then separated from the liquid phase and either the support phase or the liquid phase is examined for a detectable signal that is related to the presence of the PSA activation peptide.

Means for producing a detectable signal include the use of radioactive labels, fluorescent labels, enzyme labels, and so forth, as will be apparent to one skilled in the art. Examples of suitable immunoassays include radioimmunoassays, immunofluorescence methods, enzyme-linked immunoassays, and the like. Those skilled in the art will be familiar with numerous specific immunoassay formats and variations thereof which will be useful for carrying out the methods of the present invention.

Antibodies described herein may be conjugated to a solid support suitable for a diagnostic assay (e.g., beads, plates, slides or wells formed from materials such as latex or polystyrene) in accordance with known techniques. Antibodies may be conjugated to detectable elements such as radiolabels (e.g., $^{35}$S, $^{125}$I, $^{131}$I), enzyme labels (e.g., horseradish peroxidase, alkaline phosphatase), and fluorescent labels (e.g., fluorescein) in accordance with known techniques.

Diagnostic kits for carrying out the methods of the present invention may be produced in a number of ways. In one embodiment, the diagnostic kit comprises (a) an antibody or antibody fragment that specifically binds to PSA activation peptide (e.g., peptide of SEQ ID NO:1) conjugated to a solid support and a second such antibody or antibody fragment conjugated to a detectable element. The kit may also include ancillary reagents such as buffering agents and protein stabilizing agents; and may include (where necessary) other members of the detectable signal-producing system of which the detectable element is a part (e.g., enzyme substrates); agents for reducing background interference in a test, control reagents, apparatus for conducting a test, and the like, as will be apparent to those skilled in the art. A second embodiment of a test kit of the present invention comprises an antibody or antibody fragment specific for the PSA activation peptide, and a specific binding partner for the antibody conjugated to a detectable group. Ancillary agents as described above may likewise be included. The test kit may be packaged in any suitable manner, typically with all elements in a single container along with a sheet or printed instructions for carrying out the test.

The step of detecting the presence of PSA in the blood or serum of the test subject may be carried out concurrently with the methods of the present invention, as a further indication of whether or not the subject is afflicted with the disease state being assessed. Various methods of detecting PSA are known in the art; see e.g., U.S. Pat. No. 5,672,480 to Dowell et al.; U.S. Pat. No. 5,658,730 to McGill et al.; U.S. Pat. No. 5,654,161 to Tewari; U.S. Pat. No. 5,599,677 to Dowell et al.; and U.S. Pat. No. 5,501,983 to Lilja et al. (The disclosures of all U.S. Patent cited herein are intended to be incorporated herein in their entirety). The present methods may be used in conjunction with other diagnostic or screening tests designed to detect the target condition.

Use of the phrase "substantial sequence homology" in the present specification and claims means that DNA, RNA or amino acid sequences which have slight and non-consequential sequence variations from the actual sequences disclosed and claimed herein are considered to be equivalent to the sequences of the present invention. In this regard, 'slight and non-consequential sequence variations' mean that 'homologous' sequences (i.e., the sequences that have substantial sequence similarity with the DNA, RNA, or proteins disclosed and claimed herein) will be functionally equivalent to the sequences disclosed and claimed in the present invention. Functionally equivalent sequences will function in substantially the same manner to produce substantially the same compositions as the nucleic acid and amino acid compositions disclosed and claimed herein.

Use of the phrase "isolated" in the present specification and claims means that DNA, RNA, polypeptides or proteins have been separated from their in vivo cellular environments through the efforts of human beings.

Sequences having "substantial sequence similarity" refer to nucleotide sequences that share at least about 90% identity with invention nucleic acids; and amino acid sequences that typically share at least about 70%, 80%, 85%, 90% or even 95% amino acid identity with invention polypeptides. It is recognized, however, that polypeptides or nucleic acids containing less than the above-described levels of similarity arising as splice variants or generated by conservative amino acid substitutions, or by substitution of degenerate codons, are also encompassed within the scope of the present invention.

The present invention is explained below in the Examples set forth below.

EXAMPLE 1

Materials and Methods

Reagents—ECL Western blotting detection reagents were from Amersham (Arlington Heights, Ill.). RPMI Medium 1640, RPMI 1640 select amine kit, Dulbecco's phosphate buffered saline, Earls's balanced salt solution, and penicillin Streptomycin were from Gibco (Grand Island, N.Y.). Epidermal growth factor, L-glutamine were from Sigma (St. Louis, Mo.). PSA anti sera was from DAKO Corporation (Carpinteria, Calif.). Human metastatic prostate adenocarcinoma (LNCaP) cells were obtained from American Type Culture Collection (Rockville, Md.). Radiochemicals were from (DuPont/NEN). $\alpha_1$-ACT was purified as previously described (Salveson et al., *J. Biol. Chem.* 260:2432 (1985)). Urine samples were collected from the Duke University Medical Center Urology Clinic. Human prostatic tissues (normal, benign, hypertrophic, malignant) were obtained from Duke University Medical Center. Histology of each tissue was confirmed by a pathologist.

Purification of PSA—All steps were performed at 4° C. Approximately 100 g of prostate tissue was homogenized (Vitris Tempest) in 300 ml of 0.05 M Tris-Cl, 0.1 M NaCl, 0.01 M EDTA, pH 7.4. The homogenate was filtered through several layers of cheesecloth and cleared by centrifugation. The supernatant was subsequently digested with 0.1 mg/ml RNAse, 0.2 mg/ml DNAse and 0.005 M MgCl for 4 hours at 4° C. Following a 4 hour incubation the supernatant was dialyzed overnight against 0.01 M HEPES, pH 8. The next day the sample was clarified by centrifugation and applied to a Q-Sepharose FF (Pharmacia) column (2.5×20 cm) equilibrated in 0.01 M HEPES, pH 8. The charged column was washed extensively in equilibration buffer and then developed with a linear gradient (total volume of 2 liter) from 0 M NaCl to 0.4M NaCl. Fractions of 4 ml were collected and tested for PSA by western blotting. The active fractions were pooled and concentrated by ultrafiltration (Amicon) and applied to a S-200 HR gelfiltration (Pharmacia) column (2.5×150 cm) equilibrated in 50 mM HEPES, 150 mM NaCl. Fractions of 4 ml were collected and assayed for PSA by western blotting. The PSA containing fractions were pooled and dialyzed into 10 mM HEPES, pH 8 and separated on a MONO-Q 5/5 HR (Pharmacia) connected to a Pharmacia FPLC system. The column was equilibrated in 10 mM HEPES and developed using a linear gradient from 0 M NaCl to 400 mM NaCl.

Preparation of antisera—A peptide, Ala-Pro-Leu-Ile-Leu-Ser-Arg-Cys (SEQ ID NO:2), corresponding to an N-terminal activation peptide of PSA, was synthesized (Bio Synthesis, Lewisville, Tex.). The Cys is not part of the activation peptide but was added to facilitate coupling to ovalbumin by using m-Maleimidobenzoic acid-N-Hydroxysuccinimide Ester (Liu et al., *Biochemistry* 18:690 (1979); Kitagawa and Aikawa, *J. Biochem.* 79:233 (1976)).

Another peptide, Ala-Pro-Leu-Ile-Leu-Ser-Arg (SEQ ID NO:1) was synthesized using the MAP (Multiple Antigen Peptide) technique (Bio Synthesis, Lewisville, Tex.). Rabbit antisera to the activation peptide-ovalburin conjugates and the MAP activation peptide were raised in rabbits using a standard protocol known in the art.

Metabolic Labeling and Pulse-Chase Analysis—Human metastatic prostate adenocarcinoma (LNCaP) cells were maintained in RPMI Medium 1640 (RPMI) supplemented with 10% fetal bovine serum, epidermal growth factor (5 mg/500 ml), L-glutamine (150 mg/500 ml) and 1% penicillin Streptomycin in 5% $CO_2$. For standard biosynthetic radiolabeling, cells were grown in 50 mm tissue culture plates until 80% confluent. The cells were washed twice with Earls's balanced salt solution, and then incubated for 30 minutes in RPMI without fetal bovine serum and lacking the amino acids intended for subsequent use in metabolic labeling. After the addition of [$^{35}$S] Met, the cells were incubated for 5 minutes (pulse period). If the immunoprecipitated proteins were destined for radiosequence analysis [$^{35}$S] Met was added together with [$^3$H] Ile, [$^3$H] Leu or [$^3$H] Val. At the end of the labeling period, cells were promptly rinsed twice with serum free RPMI and chased with "cold" complete medium for various periods of time.

Lysis and Immunoprecipitation—The conditioned medium was collected and frozen. Cell lysates were prepared by three rapid freeze-thaw cycles in high salt buffer containing 0.5% Triton X-100 and a proteinase inhibitor cocktail. Prior to immunoprecipitation, the samples of lysates and conditioned medium were cleared by the addition of a pre-immune serum followed by the addition of protein-G Sepharose 4 FF (Pharmacia). The supernatants were incubated overnight with the relevant specific antiserum. The next day protein-G Sepharose 4 FF was added and immunoprecipitates were collected by gentle centrifugation. The immunoprecipitates were then washed several times and bound proteins were released from the protein G Sepharose 4 FF by boiling in SDS sample buffer or by 100 mM glycine-HCl (pH 2.7) before SDS-PAGE.

Protein Sequence Analysis and Amino Acid Analysis—Proteins and peptides were analyzed by automated Edman degradation in an Applied Biosystems 477A sequencer with on-line PTH analysis using an Applied Biosystems 120A HPLC system. Proteins and peptides were hydrolyzed in 6N HCl and the composition was determined using a Beckman 6300 amino acid analyzer. Both instruments were operated as recommended by the manufacturer.

Radiosequence Analysis—These analysis were performed as previously described (Salvesen and Enghild, Biochemistry 29:5304 (1990); Thogersen and Enghild, J. Biol. Chem. 270:18700 (1995)). Briefly, following immunoprecipitation and SDS-PAGE the [$^{35}$S] and [$^3$H] double labeled proteins were electrotransferred to immobilon membranes (Matsudaira, J. Biol. Chem. 262:10035 (1987)). The proteins were identified by autoradiography and bands of interest were excised and analyzed by automated Edman degradation. The anilinothiazolinone (ATZ) amino acids released after each cycle were collected and counted for [$^{35}$S] and [$^3$H] radioactivity. In the experiments destined for radiosequence analysis the metabolic labeling was performed using appropriate radioactive amino acids expected within the first 20 N-terminal residues of the mature proteins. Subsequent radiosequence analysis of the bands and release of radioactive ATZ-amino acid in the anticipated cycle of Edman degradation provided identification of the protein band.

Polyacrylamide Gel Electrophoresis—The supernatants from SDS-treated immunoprecipitates were recovered by centrifugation and run in sodium dodecyl sulfate (SDS) polyacrylamide gel electrophoresis (PAGE) in 5–15% gradient gels (Bury, J. Chromatography 213:491 (1981)). The gels were stained, destained, dried, and subjected to imaging on a PhosphorImager (Molecular Dynamics 410A). Immunoprecipitates for radiosequence analysis were transferred to PROBLOTT™ membranes. Following electrophoresis the PROBLOTT™ membranes were dried and exposed directly to X-ray film overnight at −70° C.

Protein and peptide radiolabeling—Proteins were radioiodinated using N-chloro-benzenesulfonamide (Markwell, Anal. Biochem. 125:427 (1982)) immobilized on polystyrene beads according to the instructions provided by the manufacturer (IODO-BEADS® Pierce). The activation peptide was labeled using $^{125}$I-Bolton-Hunter reagent (Bolton and Hunter, Biochem. J. 133:529 (1973)) as suggested by the manufacturer (DuPont/NEN).

Plasma Elimination Studies—This procedure has been described in detail elsewhere. Imber and Pizzo, J. Biol. chem 256:8134 (1981); Enghild et al., J. Biol. Chem. 26920159 (1994); Christensen et al., J. Biol. Chem. 270:14859 (1995). In brief, approximately 1.0 μg of radioiodinated protein or peptide was injected into the lateral tail vein of CD-1 mice. Blood samples of 25 μl were collected at timed intervals via retroorbital puncture. The initial time point, taken 5–10 seconds after injection, was considered to represent 100% radioactivity in circulation. Each preparation was studied at least in triplicate. Following the plasma elimination experiments, the mice were perfused and the organs removed and counted in a γ-counter.

Western blotting—Membranes were developed using the ECL Western blotting kit from Amersham™. Briefly, following transfer to PVDF membranes the membranes were blocked for 1 hour in 20 mM Tris-Cl, 137 mM NaCl, pH 7.6 containing 0.1% Tween (TBS-T buffer) and 5% of the supplied blocking reagents. The membrane was washed in TBS-T buffer before the primary antibody was added (1/2000 dilution). Following a 1 hour incubation the membrane was washed in TBS-T buffer and the horse radish peroxidase labeled second antibody was added (1/20,000 dilution). The membranes were incubated for 1 hour and washed with TBS-T buffer, and developed using the supplied reagent.

Enzyme-Linked Immunosorbent Assay (ELISA)—Costar 96-well RIA/EIA plates (Costar, Cambridge, Mass.) were incubated for 2 hours at 23° C. with increasing amounts of sample to be tested, in a total volume of 50 μl in PBS, pH 7.3. Wells containing known concentrations of activation peptide and $β_2$-microglobulin were simultaneously analyzed for comparison. Coated plates were washed and blocked with PBS containing 5% CARNATION® non-fat dry milk and 0.05% Tween 80 (blocking buffer) for 2 hours at 23° C. Plates were then incubated with 100 μl of activation peptide antisera diluted in blocking buffer overnight at 4° C. The next day the plates were briefly washed and incubated for 2 hours using 100 μl (1/2000 dilution) of alkaline phosphatase-coupled anti-(rabbit IgG). After washing with blocking buffer and PBS, the substrate p-nitrophenyl phosphate (1 mg/ml in 0.1 M glycine, 1 mM $MgCl_2$, 1 mM $ZnCl_2$, pH 10.4) was added. Alkaline phosphatase activity was followed kinetically at 37° C. using a THERMOmax microplate reader (Molecular Devices, Menlo Park, Calif.).

EXAMPLE 2

Results: Biosynthesis and Processing of PSA

The cDNA encoding PSA suggests an N-terminal 7 amino acid activation peptide. Lundwall and Lilja, FEBS Lett.

214:317 (1987). However, the putative activation peptide had not previously been detected in purified PSA. Schaller et al., *Eur. J. Biochem.* 170:111 (1987); Zhang et al., *Clin. Chem.* 41:1567 (1995); Sensabaugh and Blake, *J. Urol.* 144:1523 (1990); Watt et al., *Proc. Natl. Acad. Sci.* 83:3166 (1986). It was consequently not clear whether the activation peptide was removed intracellularly before the secretion as seen with granule serine proteases (Young et al., *Cell* 47:183 (1986); Lobe et al., *Science* 232:858 (1986); Sinha et al., *Proc. Natl. Acad. Sci.* 84:2228 (1987); Wilde et al., *J. Biol. Chem.* 265:2038 (1990); Salvesen and Enghild, *Biochemistry* 29:5304 (1990)) or after secretion as seen with most serine proteases. FIG. 1 provides a schematic diagram of PSA, where the arrows indicate the positions of the expected proteolytic cleavage sites. The solid bar represents the mature active PSA (sequence not shown), and a.p. indicates the activation peptide.

Figure 2A:
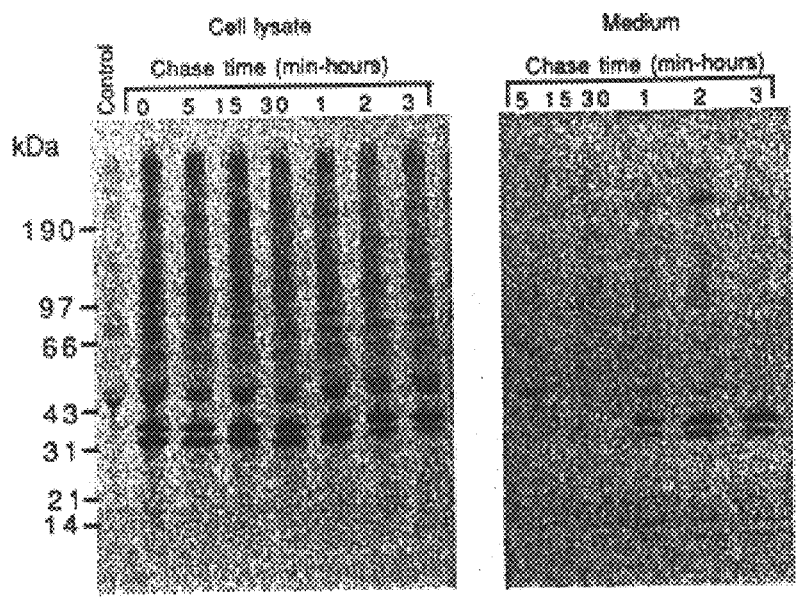
FIG. 2A provides SDS-PAGE gels of cell lysates and medium from human metastatic prostate adenocarcinoma cells that had been radiolabeled using a pulse-chase protocol. The cells were chased for the indicated times and the lysates and medium collected, and treated with specific antisera to the whole PSA; the gels indicate that the cells produce and secrete pro-PSA.
Figure 2B:
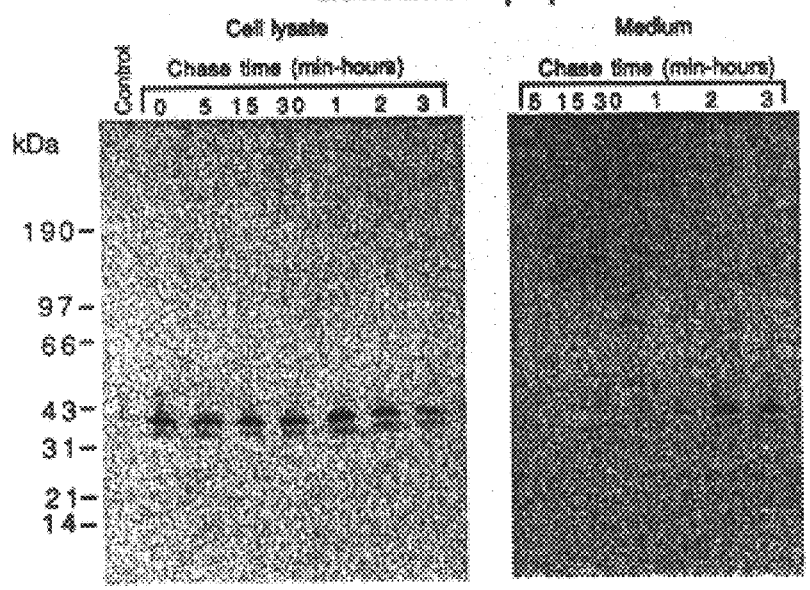
FIG. 2B provides SDA-PAGE gels as discussed above for FIG. 2A, but treated with specific antisera to the activation peptide of PSA.

To investigate the post-translational processing of PSA, the present inventors utilized biosynthetic radiolabeling and radiosequencing techniques (described in Example 1) to characterize both intracellular and secreted PSA. These analyses were performed using biosynthetically radiolabelled LNCaP cells and a polyclonal PSA antibody (FIG. 2A) and a peptide antisera specific against the activation peptide (FIG. 2B). The cells were radiolabelled using a pulse-chase protocol as described above, and the lysates and medium were collected and treated with specific antisera to the whole PSA and to the activation peptide. The samples were analyzed by reduced SDS-PAGE. Following electrophoresis, the gel was dried and subjected to imaging on a PhosphorImager. As shown, the cells produce and secrete pro-PSA.

The present results indicate that PSA does not undergo any N-terminal processing event. This was confirmed by radiosequence analysis of both intracellular and secreted PSA (data not shown). These studies establish that PSA is secreted a s an inactive pro-enzyme containing a 7-residue N-terminal activation peptide of sequence Ala-Pro-Leu-Ile-Leu-Ser-Arg- (SEQ ID NO:1). The activation of pro-PSA is an extracellular event.

EXAMPLE 3

Elimination of PSA•α1-ACT Complexes and Tissue Distribution of α1-ACT in Mouse

Figure 3:
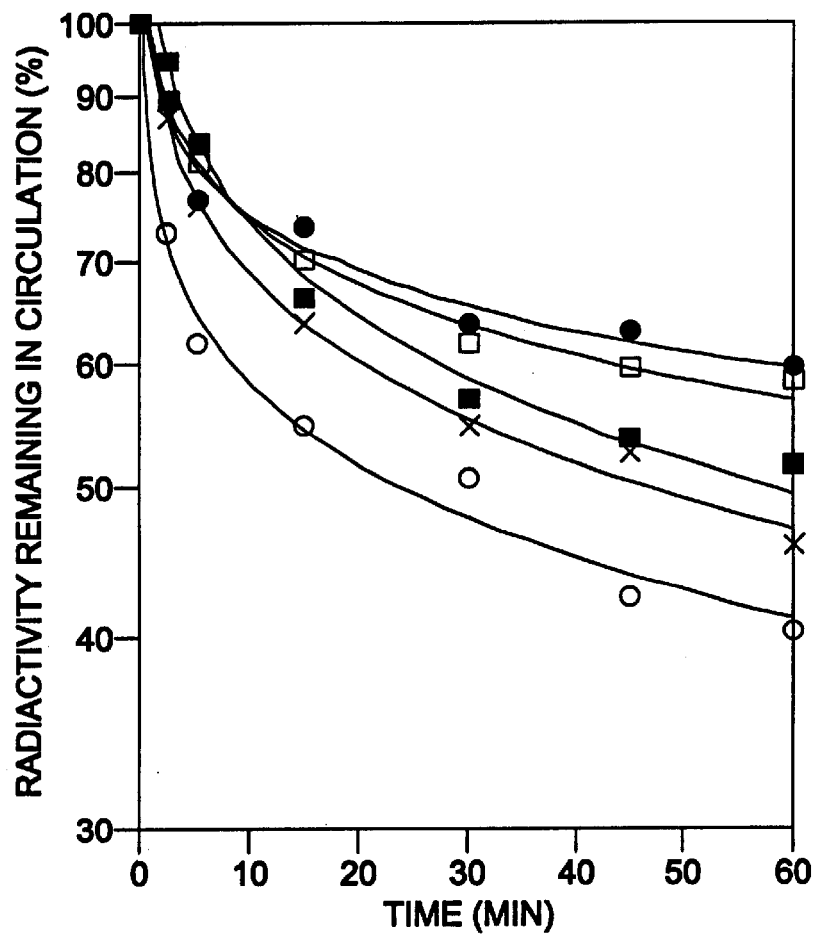
FIG. 3 graphs the plasma elimination of various forms of PSA injected into mice, where solid circles indicate the injection of radiolabelled α1-ACT; open circles indicate the injection of radiolabelled PSA•α1-ACT complex; "X" indicates the injection of radiolabelled PSA•α1-ACT complex with a 500-fold excess of unlabelled PSA•α1-ACT complex; closed squares indicate the injection of radiolabelled PSA•α1-ACT complex with a 1,000-fold excess of un-labelled PSA•α1-ACT complex; and open squares indicate the injection of radiolabelled PSA•α1-ACT complex with a 2,000-fold excess of un-labelled PSA•α1-ACT complex. The results show that the level of α1-ACT (closed circles) in the blood remains higher over time than the level of PSA•α1-ACT (in the absence of excess PSA•α1-ACT; open circles); however, as the level of PSA•α1-ACT complexes in the blood increases, PSA•α1-ACT complexes begin to accumulate in the blood.

The clearance rate of $^{125}$I-$\alpha_1$-ACT was compared to the clearance rate of $^{125}$I-$\alpha_1$-ACT•PSA complexes in mice, using techniques as described above. As shown in FIG. 3, comparing $\alpha_1$-ACT injected alone (solid circles) and $\alpha_1$-ACT in complex with PSA (open circles) shows that the half life of the PSA•α1-ACT complex was significantly reduced compared to native α1-ACT. To mimic a situation in which more PSA is sereted, $^{125}$I-PSA•α1-ACT complex was injected with a 500-fold (X), 1000-fold (solid squares) and 2000-fold (open squares) excess of 'cold' PSA•α1-ACT complexes. These experiments showed that PSA•α1-ACT complex is initially removed from the blood, and that as the level of PSA•α1-ACT complex increases in the blood the clearance mechanism becomes saturated and PSA•α1-ACT complexes begin to accumulate in the blood.

Thestuie shwed that the $^{125}$I-$\alpha_1$-ACT•PSA complexes were removed from the mouse circulation with a half-life of approximately 20 minutes; the half life of $^{125}$I-$\alpha_1$-ACT was estimated to be several hours. To investigate if the accumulation of $\alpha_1$-ACT•PSA complexes in the blood were caused by a saturation of the clearance mechanism, $^{125}$I-$\alpha_1$-ACT•PSA complexes were coinjected with a large excess of unlabeled $\alpha_1$-ACT•PSA complexes. The half life increased from approximately 20 minutes to several hours. These experiments show that clearance rate is significantly affected by the level of $\alpha_1$-ACT•PSA complex in the blood stream and indicate that the accumulation of $\alpha_1$-ACT•PSA in the blood is caused by a saturation of the clearance mechanism.

Figure 4:
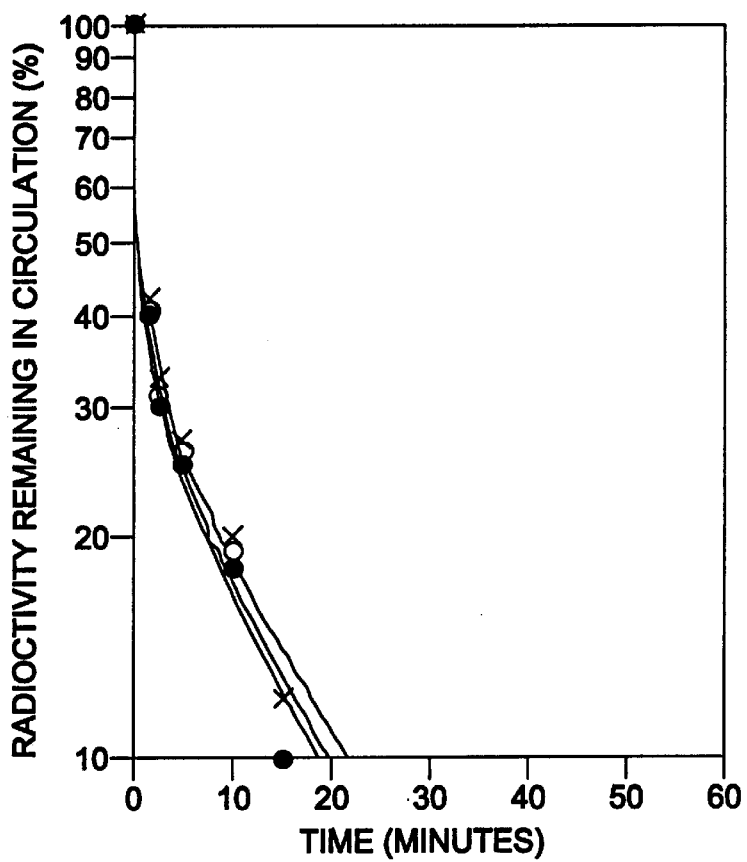
FIG. 4 graphs the plasma elimination of PSA activation peptide in mice, where closed circles indicate the injection of $^{125}$I-labelled PSA activation peptide; open circles indicate injection of $^{125}$I-labelled PSA activation peptide in conjunction with a 1,000-fold excess of unlabelled activation peptide; and "X" indicates injection of $^{125}$I-labelled PSA activation peptide in conjunction with a 2,000-fold excess of unlabelled activation peptide. The half-life of the activation peptide was not significantly affected by the amount of peptide injected.

Plasma elimination of the activation peptide was studied by injecting $^{125}$I labeled activation peptide (Ala-Pro-Leu-Ile-Leu-Ser-Arg; SEQ ID NO:1) into the lateral tail vein of a mouse. Plasma elimination of $^{125}$I labeled activation peptide was followed for 1 hour (solid circles, FIG. 4); the half-life of the peptide was less than 2 minutes. The $^{125}$I labeled activation peptide was also injected with a 1000-fold (open circles) and 2000-fold (X) excess of un-labelled activation peptide. The clearance rate was not significantly affected by the level of activation peptide in the blood stream.

Figure 5:
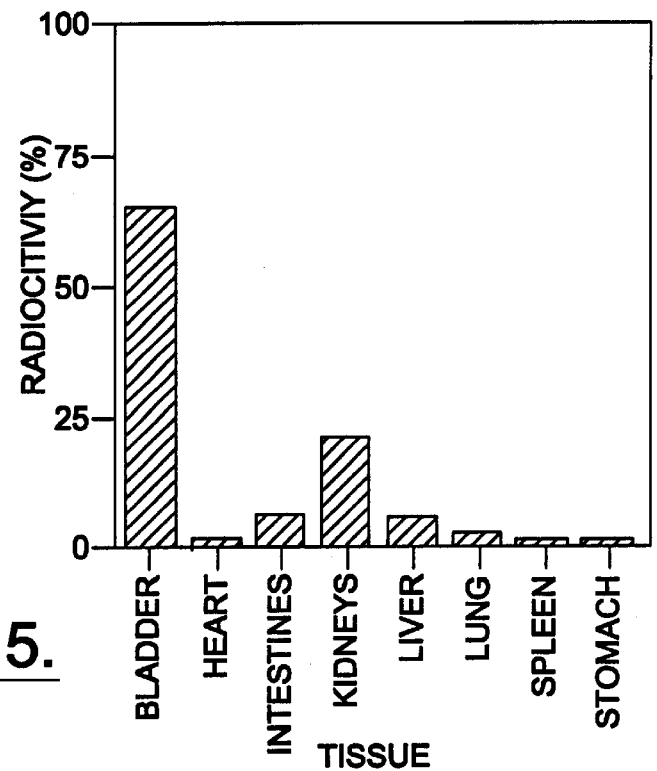
FIG. 5 graphs the relative tissue distribution of $^{125}$I-labelled PSA in mice.

Following the plasma elimination experiments the organs of the test mice were examined for radioactivity using a γ-counter. The predominance of $\alpha_1$-ACT in bladder and kidney indicates that the peptide is removed from the blood stream by renal filtration (FIG. 5).

The above results indicate that at initial levels, PSA•α1-ACT complexes are cleared rapidly from the bloodstream of mammals; however, as more PSA•α1-ACT complexes are introduced into the bloodstream, the clearance mechanism is saturated, leading to an excess of PSA•α1-ACT complexes in the bloodstream.

EXAMPLE 4

Detection of PSA Activation Peptide in Biological Samples

Figure 6A:
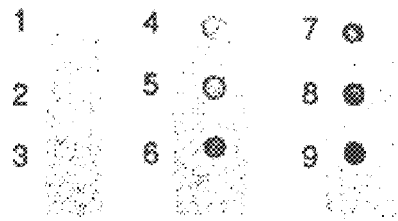
FIG. 6A shows the detection of increasing concentrations of PSA activation peptide, using antisera to the activation peptide. The concentration of the peptide was increased from 0.01 ng of peptide in well #1, to 5.0 ng of peptide in well #9.

The results provided above indicate that the PSA activation peptide that is cleaved from PSA is cleared from the bloodstream by renal filtration, and is present in urine and in the blood. To test whether PSA activation peptide is measurable in the urine or serum of patients with benign prostatic hypertrophy or prostate cancer, the activation peptide of SEQ ID NO:1 was synthesized and a polyclonal peptide antisera was prepared in rabbits. The specificity of the antisera was verified by ELISA against the synthetic activation peptide, which was provided in amounts ranging from 0.01–5.0 ng of peptide (FIG. 6A; increasing concentration of activation peptide from dot 1 to dot 9). The antisera produced a dose-dependent sensitive reaction.

Figure 6B:
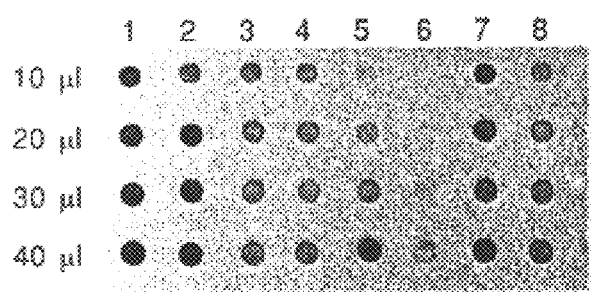
FIG. 6B shows the detection of PSA activation peptide using antisera, in urine samples from eight subjects previously diagnosed with prostate cancer.
Figure 6C:
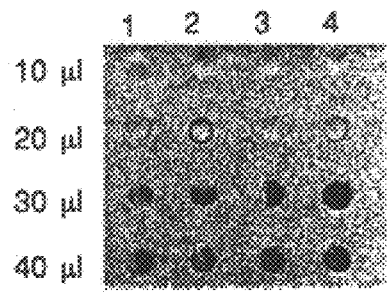
FIG. 6C shows the detection of PSA activation peptide using antisera, in blood serum samples from four subjects previously diagnosed with prostate cancer.
Figure 6D:
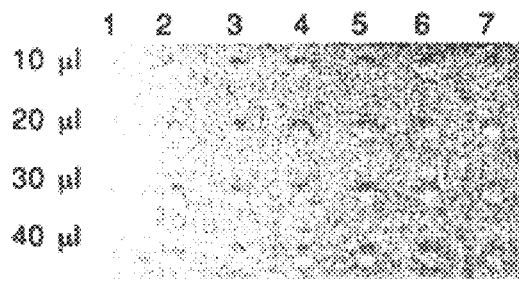
FIG. 6D shows the detection of PSA activation peptide using antisera, in urine samples from seven control subjects without prostate disease.
Figure 6E:
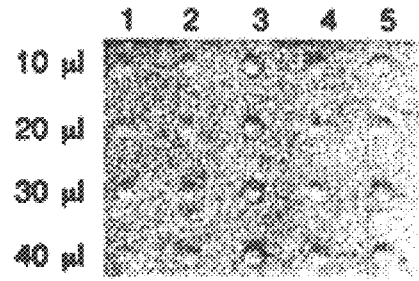
FIG. 6E shows the detection of PSA activation peptide using antisera, in blood serum samples from five control subjects without prostate disease.

Serum and urine samples from control patients (no prostate disease) and patients with prostate cancer were obtained and tested for the presence of the activation peptide as discussed above. The activation peptide was detected in the urine (FIG. 6B) and serum (FIG. 6C) of the cancer patients, but not in the urine (FIG. 6D) or serum (FIG. 6E) of controls.

These results indicate that detection of PSA activation peptide in the urine or serum of subjects is feasible and indicates the presence of PSA.

EXAMPLE 5

Biotinylation of PSA Activation Peptide

PSA Activation peptide containing an added C-terminal Cys residue (Ala-Pro-Leu-Ile-Leu-Ser-Arg-Cys; SEQ ID NO:2) was biotinylated using N-(6-[biotinamido])hexyl)-3'-(2'-pyridyldithio)propionamide(Pierce). This reagent can be used in a standard ELISA assay as follows:

1) coat a 96-well ELISA plate with anti-activation peptide antiserum and block residual binding sites (PBS containing 0.05% Tween 20 and 0.25% bovine serum albumin (BSA));

2) add a fixed concentration of biotinylated PSA activation peptide and increasing amounts of sample (e.g., urine, blood, blood serum) to a series of wells, 3) wash the wells before adding avidin and biotinylated horseradish peroxidase;

4) after incubation, wash the wells and detect residual biotinylated PSA activation peptide in a plate reader at 450 nm using the horseradish peroxidase substrate TURBO 3,3',5,5'-Tetramethyl Benzidine (TMB) (Pierce).

The foregoing examples are illustrative of the present invention, and are not to be construed as limiting thereof. The invention is described by the following claims, with equivalents of the claims to be included therein.

That which is claimed is:

1. A method of screening a subject for secreted Prostate Specific Antigen (PSA), comprising:
    (a) obtaining a biological sample from a subject; and
    (b) detecting the amount of PSA activation peptide in said sample; the detection of PSA activation peptide in said sample indicating the presence of secreted PSA in said subject;
    said PSA activation peptide consisting of SEQ ID NO:1.

2. A method according to claim 1, further comprising comparing the amount of peptide detected to a pre-established standard.

3. A method according to claim 1 where said biological sample is urine.

4. A method according to claim 1 where said biological sample is selected from the group consisting of blood, blood plasma or blood serum.

5. A method according to claim 1 where said detecting step is carried out by immunoassay.

6. A method of screening a subject for the presence of a condition associated with an increased level of secreted Prostate Specific Antigen (PSA), comprising:
    (a) obtaining a biological sample from a subject;
    (b) detecting the amount of PSA activation peptide in said sample; and
    (c) comparing said amount of peptide detected to a predetermined standard, where detection of a level of peptide greater than that of the standard indicates the presence of said condition;
    said PSA activation peptide consisting of SEQ ID NO:1; and
    said condition selected from the group consisting of prostate cancer, Benign Prostate Hypertrophy, and breast cancer.

7. A method according to claim 6 where said biological sample is urine.

8. Method according to claim 6 where said biological sample is blood, blood plasma or blood serum.

9. A method according to claim 6 where said subject has not previously been diagnosed with prostate cancer.

10. A method of screening a subject for prostate disease, comprising:
    (a) obtaining a urine sample from said subject; and
    (b) quantifying the level of PSA activation peptide in said sample, said PSA activation peptide consisting of SEQ ID NO:1; where the quantification of said PSA activation peptide in said sample is indicative of prostate disease in said subject.

11. A method according to claim 10, further comprising the step of comparing the level of quantified peptide to a standard, where prostate disease is indicated when the level of quantified peptide is greater than the standard.

12. A method according to claim 10 where said quantification step is carried out by immunoassay.

13. A method according to claim 12 where said immunoassay is selected from radioimmunoassays and enzyme-linked immunoassay.

14. A method according to claim 10 where said biological sample is urine.

15. A method according to claim 10 where said biological sample is blood, blood plasma or blood serum.

16. A method according to claim 10 where said subject has not previously been diagnosed with prostate disease.

17. A method according to claim 10, wherein said prostate disease is benign prostate hypertrophy.

18. A method according to claim 10, wherein said prostate disease is prostate cancer.

19. An immunoassay method for determining the presence of a peptide consisting of SEQ ID NO:1 in a sample, comprising:
 (a) obtaining a test sample;
 (b) exposing said sample to an antibody specific for a peptide consisting of SEQ ID NO:1; and
 (c) detecting the binding of said antibody to peptides present in said sample;
wherein said binding of antibodies indicates the presence of peptides consisting of SEQ ID NO:1 in the sample.

20. A method according to claim 19 where said sample is urine.

21. A method according to claim 19 where said sample is blood or blood serum.

22. A method of screening for prostate cancer in a subject, comprising:
 (a) obtaining a biological sample from said subject, said sample selected from the group consisting of urine, blood, blood plasma and blood serum; and
 (b) quantifying the level of Prostate Specific Antigen (PSA) activation peptide in said sample; where the quantification of PSA activation peptide in said sample is indicative of prostate cancer in said subject;
 said PSA activation peptide consisting of SEQ ID NO:1.

23. A method according to claim 22 further comprising comparing the quantified level of PSA activation peptide to a standard, where a level greater than that of the standard is indicative of prostate cancer.

24. A method according to claim 22 where said detecting step is carried out by immunoassay.

25. A method according to claim 24 where said immunoassay is selected from radioimmunoassay and enzyme-linked immunoassay.

26. A method according to claim 22 where said biological sample is urine.

27. A method according to claim 22 where said subject has not previously been diagnosed with prostate disease.

28. An isolated peptide consisting of SEQ ID NO:1.

* * * * *